US009944018B2

(12) United States Patent
Kuroda et al.

(10) Patent No.: US 9,944,018 B2
(45) Date of Patent: Apr. 17, 2018

(54) METHOD FOR PRODUCING COMPOSITE MEMBER

(71) Applicant: GUNZE LIMITED, Kyoto (JP)

(72) Inventors: Kouji Kuroda, Shiga (JP); Syouichi Tsukada, Shiga (JP); Shuhei Ogami, Shiga (JP); Satoshi Mukai, Shiga (JP)

(73) Assignee: GUNZE LIMITED, Kyoto (JP)

( * ) Notice: Subject to any disclaimer, the term of this patent is extended or adjusted under 35 U.S.C. 154(b) by 696 days.

(21) Appl. No.: 14/386,915

(22) PCT Filed: Feb. 25, 2013

(86) PCT No.: PCT/JP2013/054676
§ 371 (c)(1),
(2) Date: Feb. 6, 2015

(87) PCT Pub. No.: WO2013/140944
PCT Pub. Date: Sep. 26, 2013

(65) Prior Publication Data
US 2015/0136310 A1 May 21, 2015

(30) Foreign Application Priority Data
Mar. 23, 2012 (JP) .................... 2012-068305

(51) Int. Cl.
B29C 65/46 (2006.01)
B29C 53/60 (2006.01)
(Continued)

(52) U.S. Cl.
CPC ............... *B29C 65/46* (2013.01); *B05D 1/02* (2013.01); *B05D 3/0281* (2013.01); *B21F 17/00* (2013.01);
(Continued)

(58) Field of Classification Search
CPC ... B29C 65/46; B29C 66/742; B29C 66/7428; B29C 66/74281; B29C 66/74283;
(Continued)

(56) References Cited

U.S. PATENT DOCUMENTS 3,607,516 A * 9/1971 Royston ............... F16L 58/16
156/187
5,244,587 A 9/1993 Ito et al.
(Continued)

FOREIGN PATENT DOCUMENTS

JP H04-126561 A 4/1992
JP H05-339664 A 12/1993
(Continued)

OTHER PUBLICATIONS

International Search Report; PCT/JP2013/054676; dated Jul. 2, 2013.

Primary Examiner — Carson Gross
(74) Attorney, Agent, or Firm — Studebaker & Brackett PC

(57) ABSTRACT

The invention provides a novel method for producing a composite member by fixing a surface member to the outer peripheral surface of a core member. A method for producing a composite member having a core member and a surface member fixed to the outer peripheral surface of the core member includes the surface member providing step of providing the surface member having magnetism lower than magnetism of the core member made of a conductive material on the outer peripheral surface of the core member, and the fusing step of electromagnetic induction heating the core member from outside the surface member to melt at least one of facing regions between the surface member and the core member with heat of the heated core member and fuse the surface member to the core member.

9 Claims, 5 Drawing Sheets

(51) Int. Cl.
*C09J 5/06* (2006.01)
*B21F 17/00* (2006.01)
*B21F 45/00* (2006.01)
*B21F 99/00* (2009.01)
*B05D 1/02* (2006.01)
*B05D 3/02* (2006.01)
*B32B 37/04* (2006.01)
*B32B 37/12* (2006.01)
*B32B 37/14* (2006.01)
*B32B 38/00* (2006.01)
*B65H 54/00* (2006.01)
*B29L 31/00* (2006.01)
*B29C 65/00* (2006.01)
*A61M 25/09* (2006.01)

(52) U.S. Cl.
CPC .............. *B21F 45/00* (2013.01); *B21F 99/00* (2013.01); *B29C 53/60* (2013.01); *B32B 37/04* (2013.01); *B32B 37/1284* (2013.01); *B32B 37/142* (2013.01); *B32B 38/0008* (2013.01); *C09J 5/06* (2013.01); *A61M 2025/09108* (2013.01); *B29C 66/69* (2013.01); *B29C 66/71* (2013.01); *B29C 66/742* (2013.01); *B29C 66/74283* (2013.01); *B29C 66/836* (2013.01); *B29L 2031/753* (2013.01); *B65H 54/00* (2013.01); *C09J 2205/31* (2013.01)

(58) Field of Classification Search
CPC ... B05D 3/0281; B29L 2031/34; B21F 17/00; B65H 54/00
USPC ............ 156/51–53, 172, 187, 188, 191, 195
See application file for complete search history.

(56) References Cited

U.S. PATENT DOCUMENTS

| | | | |
|---|---|---|---|
| 5,599,633 A | | 2/1997 | Miyazaki et al. |
| 5,700,530 A | * | 12/1997 | Van Beersel ....... B29C 53/8083 156/195 |
| 2008/0028592 A1 | * | 2/2008 | Stieler ................. B29C 65/3656 29/447 |
| 2011/0159192 A1 | * | 6/2011 | Daykin ............... B05B 13/0436 427/314 |

FOREIGN PATENT DOCUMENTS

| | | |
|---|---|---|
| JP | 2003-148454 A | 5/2003 |
| JP | 2003-289616 A | 10/2003 |
| JP | 2008-125628 A | 6/2008 |

* cited by examiner

[Fig.1]
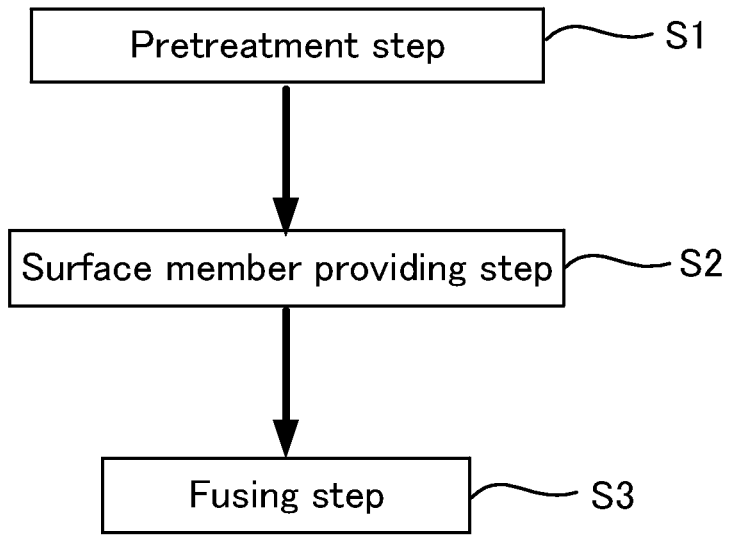
[Fig.2]
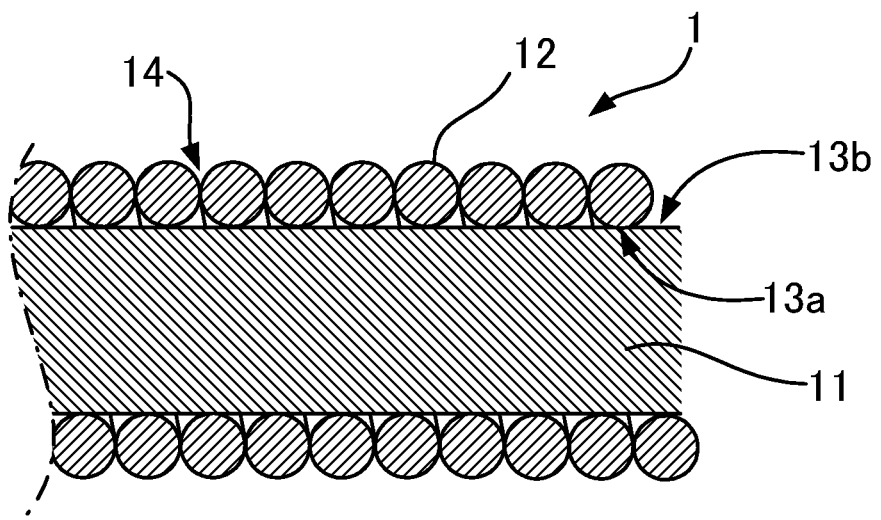

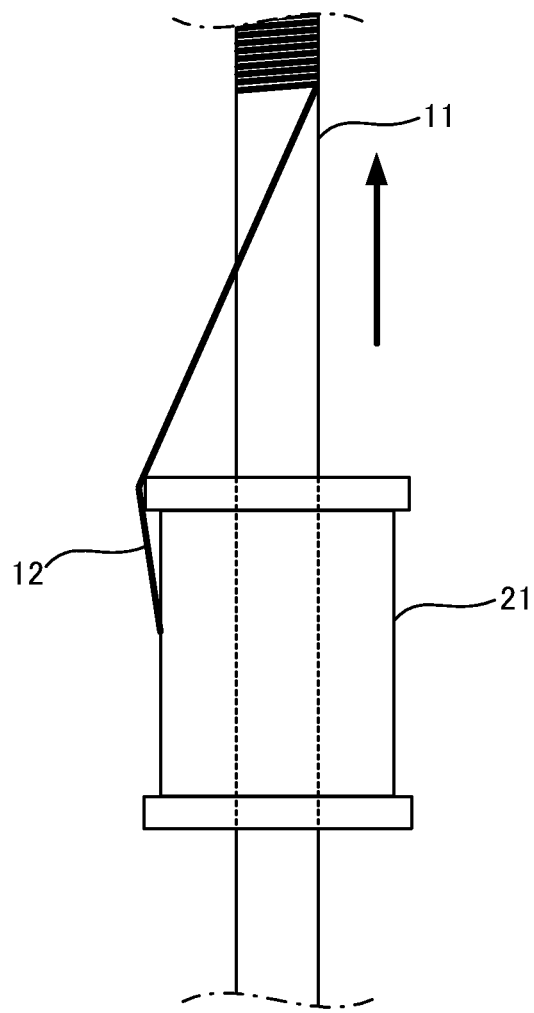
[Fig.3]

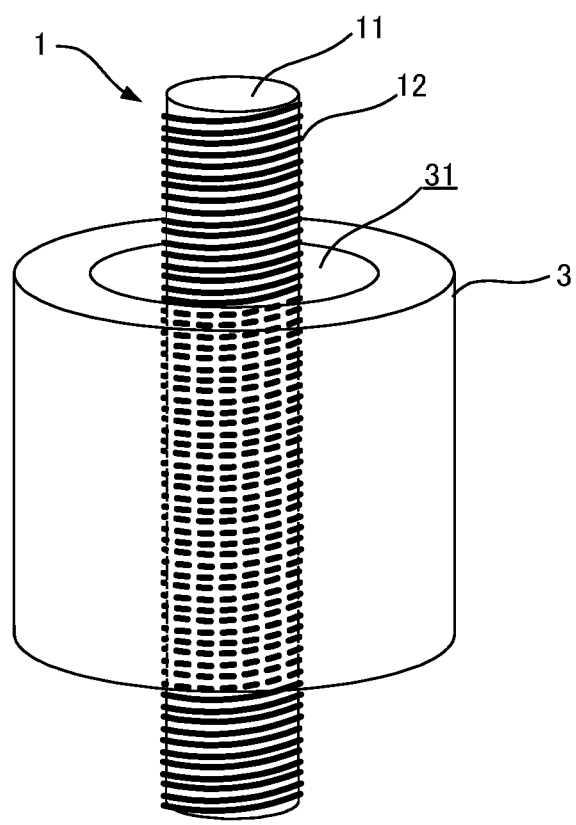
[Fig.4]

[Fig.5]
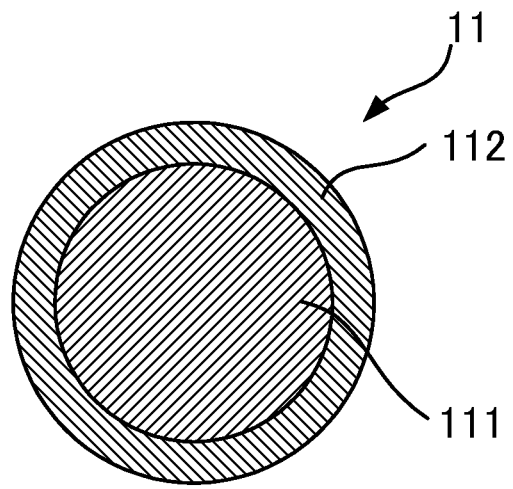
[Fig.6]
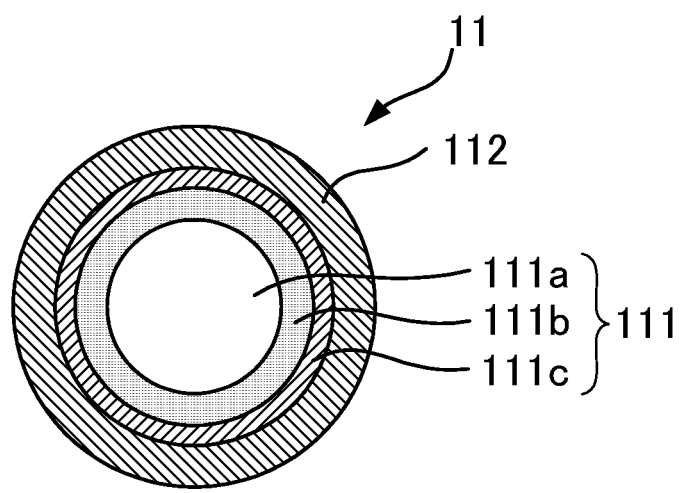

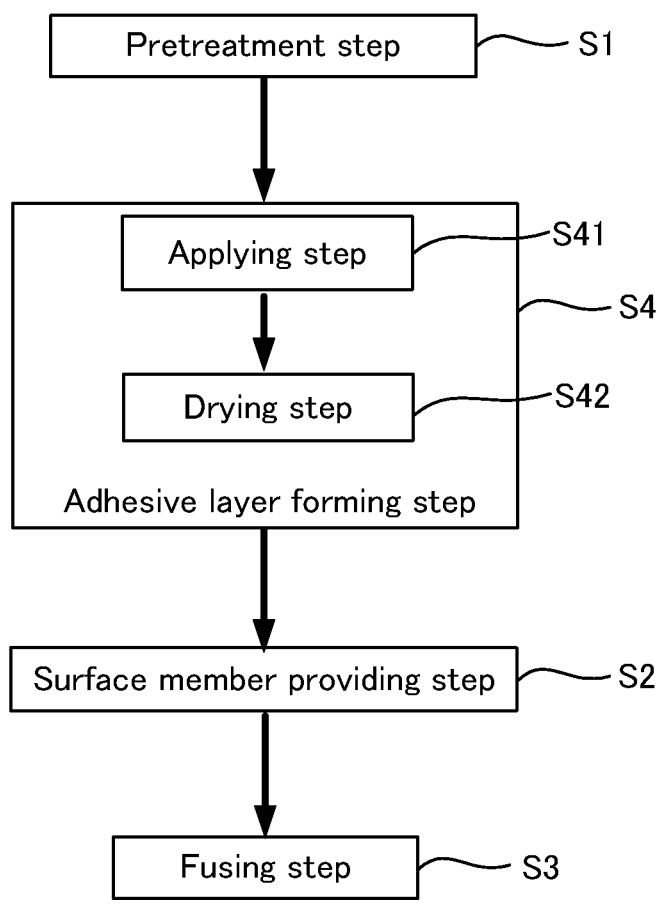

METHOD FOR PRODUCING COMPOSITE MEMBER

TECHNICAL FIELD

The present invention relates to a method for producing a composite member. The present invention relates particularly to a method for producing a composite member by fixing a surface member to the outer peripheral surface of a core member.

BACKGROUND ART

A conventionally known tool includes any one of various composite members produced by providing, on the outer surface of a member serving as a core member, a cover layer made of a material different from that for the core member. Examples of such a known tool include various tools such as a medical guide wire used in intravascular treatment, an electrode wire used in electric discharge machining, and a heat insulating pipe.

The medical guide wire used in intravascular treatment is produced by covering the surface of a linear metal core member with a resin and applying hydrophilization treatment to the surface of the resin (e.g. Patent Document 1). Various techniques can be adopted for covering the surface of the core member with a resin. For example, a known method includes immersing the linear core member in a reservoir containing a resin generated in a liquid form at high temperature and then cooling to form a resin layer on the surface of the linear core member.

The electrode wire used in electric discharge machining is produced by covering the periphery of a core member made of Cu alloy with a Cu—Zn alloy layer, for example (e.g. Patent Document 2). A method for plating with Zn the surface of the core member is known as a technique for forming the Cu—Zn alloy layer on the surface of the core member.

There are heat insulating pipes in various forms. For example, a heat insulating pipe used for preventing heat radiation and supplying liquid is produced by winding a heat insulating member in a sheet shape around the outer peripheral surface of a metal pipe.

PRIOR ART DOCUMENTS

Patent Documents

Patent Document 1: JP 2008-125628 A
Patent Document 2: JP 5-339664 A

SUMMARY OF THE INVENTION

Problems to be Solved by the Invention

As described above, there have been devised various methods for producing a desired composite member by providing, on the outer surface of a member serving as a core member, a cover layer made of a material different from that for the core member. An object of the present invention is to provide a novel production method completely different from these production methods, particularly a novel method for producing a composite member by fixing a surface member to the outer peripheral surface of a core member.

Means for Solving the Problems

The object of the present invention is achieved by a method for producing a composite member including a core member and a surface member fixed to an outer peripheral surface of the core member, the method including: a surface member providing step of providing the surface member having magnetism lower than magnetism of the core member made of a conductive material on the outer peripheral surface of the core member; and a fusing step of electromagnetic induction heating the core member from outside the surface member to melt at least one of facing regions between the surface member and the core member with heat of the heated core member and fuse the surface member to the core member.

According to such a method for producing the composite member, the melted portion corresponds to at least one of the facing regions between the surface member and the core member (the facing region in the surface member with respect to the core member, the facing region in the core member with respect to the surface member, or the both thereof). The surface member can be thus fused and fixed securely onto the outer peripheral surface of the core member with no damage in shape of the outer surface of the surface member by thermal melting. Even when a material hardly generated in a liquid form upon provision of the surface member on the outer peripheral surface of the core member is selected for the surface member, the surface member formed into a linear shape or particle shapes can be fused onto the outer peripheral surface of the core member.

In this method for producing the composite member, the surface member preferably has a melting point lower than a melting point of the core member.

The surface member provided on the outer peripheral surface of the core member is made of a material having the melting point lower than that of a material for the core member in this manner. The facing region in the surface member with respect to the core member can be melted earlier than the core member with heat of the core member electromagnetic induction heated. In this case, only the surface member can be melted reliably with no damage in shape of the core member by thermal melting so as to be fused and fixed onto the outer peripheral surface of the core member.

For the object of the present invention, preferably, the core member has a center portion and a surface portion, and the surface portion of the core member is melted with heat of the core member electromagnetic induction heated to fuse the surface member to the core member.

According to such a method for producing the composite member, thermally melted is the surface portion of the core member corresponding to the facing region in the core member with respect to the surface member. The surface member can be thus fused and fixed securely onto the outer peripheral surface of the core member with no damage in shape of the outer surface of the surface member by thermal melting.

The method preferably includes, prior to the surface member providing step, an adhesive layer forming step of applying an adhesive having a melting point lower than a melting point of the core member to the outer peripheral surface of the core member.

In this manner, after the adhesive having the melting point lower than the melting point of the core member is applied to the outer peripheral surface of the core member, the surface member is provided on the outer peripheral surface of the core member and the core member is electromagnetic induction heated from outside the surface member. In an exemplary case where the surface member has a melting point lower than the melting point of the core member and the adhesive used by an adhesive layer forming means has a melting point substantially not more than the melting point of the surface member, the adhesive provided in the facing region in the surface member with respect to the core member and between the surface member and the core member can be melted by heating the core member. The surface member can be thus fixed more firmly to the core member. Specifically, when the surface member is made of a linear material spirally wound around the outer peripheral surface of the core member or is formed into particle shapes or fiber shapes so as to be sprayed to and provided on the outer peripheral surface of the core member, the melted adhesive enters gaps between adjacent portions of the linear material or the adjacent particles, so that the surface member can be fixed securely to the core member.

The adhesive layer forming step preferably includes a drying step of drying the adhesive applied to the outer peripheral surface of the core member.

When the adhesive applied to the outer peripheral surface of the core member is dried prior to provision of the surface member on the outer peripheral surface of the core member in this manner, the surface member can be provided on the outer peripheral surface of the core member with the adhesive having no adhesive force. The surface member can be alternatively provided on the outer peripheral surface of the core member even with active adhesive force of the adhesive, in other words, even in a state where the adhesive is not dried. However, when the surface member is provided on the outer peripheral surface of the core member with the adhesive being not dried but in a liquid state or a semiliquid state, the adhesive in the liquid state (or the semiliquid state) may leak from around the provided surface member and remain on the outer surface of the composite member finally obtained. Otherwise, the adhesive in the liquid state (or in the semiliquid state) may flow along the outer peripheral surface of the core member and fail to be distributed uniformly on the outer peripheral surface of the core member. If electromagnetic induction heating is performed in such a case, the surface member and the core member may be fixed to each other with less force at a portion on the surface of the core member to which the adhesive is applied with less thickness when the adhesive and/or the facing region in the surface member with respect to the core member is melted and the surface member is fixed to the core member. In contrast, when the adhesive applied to the outer peripheral surface of the core member is dried prior to provision of the surface member on the outer peripheral surface of the core member and the surface member is then provided on the outer peripheral surface of the core member, the states described above (leak of the adhesive and ununiform distribution of the adhesive) can be effectively prevented. The adhesive can be reliably prevented from remaining on the outer surface of the composite member finally obtained, or a portion of less fixing force between the surface member and the core member can be reliably prevented from being generated.

The surface member providing step preferably includes a covering step of winding the surface member made of a linear material around the outer peripheral surface of the core member to cover the outer peripheral surface of the core member with the surface member. The surface member providing step preferably includes a covering step of spraying the surface member formed into particle shapes or fiber shapes to the outer peripheral surface of the core member to cover the outer peripheral surface of the core member with the surface member.

Effects of the Invention

The present invention can provide a novel method for producing a composite member by fixing a surface member to the outer peripheral surface of a core member.

BRIEF DESCRIPTION OF THE DRAWINGS

FIG. 1 is a block diagram showing steps in a method for producing a composite member according to an embodiment of the present invention.

FIG. 2 is a sectional diagram of the composite member produced by the production method according to the present invention.

FIG. 3 is a schematic configuration diagram of a covering device that is used in a surface member providing step included in the method for producing the composite member according to the embodiment of the present invention.

FIG. 4 is a schematic configuration diagram of an electromagnetic induction heating device that is used in a fusing step included in the method for producing the composite member according to the embodiment of the present invention.

FIG. 5 is a schematic configuration sectional diagram exemplifying a core member that is used in the method for producing the composite member according to the present invention.

FIG. 6 is a schematic configuration sectional diagram exemplifying a core member different from that shown in FIG. 5.

FIG. 7 is a block diagram showing steps in a method for producing a composite member according to a different embodiment of the present invention.

EMBODIMENTS OF THE INVENTION

A method for producing a composite member according to each embodiment of the present invention, by fixing a surface member to the outer peripheral surface of a core member, will now be described with reference to the accompanying drawings. FIG. 1 is a block diagram showing steps in a method for producing a composite member 1 according to an embodiment of the present invention. As illustrated in FIG. 1, the method for producing the composite member 1 according to the present invention includes a pretreatment step S1, a surface member providing step S2 to be executed after the pretreatment step S1, and a fusing step S3 to be executed after the surface member providing step S2.

As illustrated in the sectional diagram of FIG. 2, the composite member 1 produced by the production method according to the present invention includes a core member 11 serving as a core and a surface member 12 fixed to the outer peripheral surface of the core member 11. FIG. 2 is a sectional diagram taken along the axis of the composite member 1. The core member 11 is made of a conductive material. The core member 11 is not particularly limited in terms of its shape, but can have any one of various shapes including a bar shape, a linear shape, a columnar shape, and a hollow cylindrical shape. The core member 11 can be made of a single material or can be made of a plurality of materials so as to exhibit its functions. The core member 11 made of a plurality of materials can be configured variously, e.g. including two different linear metal members twisted together, including a linear metal member and a linear resin member twisted together, or including a center portion and a surface portion made of different materials (a member having a double layer structure including a center portion made of metal and a surface portion made of a thermosetting resin coated on the outer surface of the center portion, for example). When the core member 11 is made of a plurality of materials, at least one of the materials is likely to conduct electricity so that the entire core member 11 has conductivity.

The surface member 12 is made of a material having magnetism lower than that of the core member 11. Such materials having magnetism lower than that of the core member 11 conceptually include a material having magnetism weaker than that of the core member 11 as well as a material having no magnetism. The surface member 12 can be made of a material that is likely to conduct electricity, or can be made of a material that does not conduct electricity. The surface member 12 can be made of a metal material such as iron or stainless steel, or can be made of a synthetic resin material. Preferable examples of the synthetic resin material include fluorine resins, polyester resins, polyamide resins, and polyolefin resins. The surface member 12 is also particularly unlimited in terms of its shape as long as the surface member 12 can be provided on the outer peripheral surface of the core member 11. The surface member 12 can have any one of various shapes such as a linear shape, particle shapes, a belt shape, and fiber shapes. The material for the surface member 12 can be appropriately selected in accordance with the function to be provided to the composite member 1 (such as a corrosion-resistant function, a lubricant function, a thermally insulating function, or a fatigue resistant function). In an exemplary case where the surface member 12 is to be provided with one of the corrosion-resistant function, the lubricant function, the thermally insulating function, and the fatigue resistant function, a material suitable for provision of the desired function can be selected to configure the surface member 12. In another case where the surface member 12 is to be provided with a plurality of functions at one time, a plurality of materials respectively exhibiting the desired functions can be selected to configure the surface member 12.

The pretreatment step S1 includes any one of various treatments such as foreign matter removal of removing dirt, dust, or the like adhering to the outer peripheral surface of the core member 11, grease removal of removing an oil composition such as mineral oil adhering to the outer peripheral surface of the core member 11, and surface processing performed for improvement in adhesion between the outer peripheral surface of the core member 11 and the surface member 12. The pretreatment step S1 can include a single treatment selected from the foreign matter removal, the grease removal, and the surface processing, or can include a plurality of treatments. Examples of the foreign matter removal can include air processing of blowing air to the core member 11 to remove dirt or dust adhering to the outer peripheral surface thereof, water washing of washing the core member 11 with water to remove dirt, and wipe processing of wiping, with waste cloth or the like, dirt and the like on the outer peripheral surface of the core member 11. Examples of the grease removal can include grease removal using a solvent of immersing the core member 11 in a grease removing process liquid such as alcohol, acetone, or paint thinner in a grease removing vessel to remove an oil composition such as mineral oil or dirt adhering to the core member 11. The grease removal can be achieved by not only such grease removal using a solvent but also by various grease removing techniques including grease removal through heating, of heating to remove an oil composition on the surface of the core member 11, ultrasonic grease removal using a shock wave generated upon bursting vacuum bubbles generated in a liquid by an ultrasonic wave, and grease removal through alkaline electrolysis, of immersing the core member 11 in an alkaline cleaning liquid and applying electrolysis of predetermined current density to remove an oil composition such as mineral oil adhering to the surface of the core member 11. Examples of the surface processing can include blast processing for improvement in unevenness of the outer peripheral surface of the core member 11. The pretreatment step S1 improves adhesive strength between the core member 11 and the surface member 12 in the surface member providing step S2 to be described later. The production method according to the present invention can be accomplished without including the pretreatment step S2 in a case where sufficient adhesive strength between the core member 11 and the surface member 12 can be achieved with no execution of the pretreatment step S1.

The surface member providing step S2 is executed to provide the surface member 12 having magnetism lower than that of the core member 11 made of a conductive material on the outer peripheral surface of the core member 11, and is executed after the pretreatment step S1. The surface member providing step S2 can be executed by any one of various methods for providing the surface member 12 on the outer peripheral surface of the core member 11. Described below is an exemplary method for spirally winding the surface member 12 made of a linear material around the outer peripheral surface of the core member 11 to cover the outer peripheral surface of the core member 11 with the surface member 12 (the covering step). The covering step is executed using a covering device 2 shown in FIG. 3. The covering device 2 includes a spool 21 having a shaft and a linear material wound around the shaft, and a drive unit (not shown) for rotating the spool 21 about the shaft. The shaft of the spool 21 is formed to be hollow so that the core member 11 can be inserted to the hollow portion. The covering device 2 operates in the following manner. The linear material (the surface member 12) wound at the spool 21 is initially led out and the tip of the linear material (the surface member 12) is fixed to the surface of the core member 11. The spool 21 is then rotated by the drive unit and the core member 11 is shifted (along the shaft of the spool 21) at a predetermined speed by a conveying means (not shown) provided separately. The linear material serving as the surface member 12 is thus spirally wound around the outer peripheral surface of the core member 11 and the outer peripheral surface of the core member 11 is covered with the surface member 12 made of the linear material as illustrated in FIG. 2. Appropriately adjusting the speed of conveying (shifting) the core member 11 by the conveying means or the number of rotation of the spool 21 enables adjustment of density (the number of winding of the linear material per unit length of the core member 11) of the surface member 12 made of the linear material wound around the outer peripheral surface of the core member 11.

The fusing step S3 is executed to fuse the surface member 12 to the core member 11 by electromagnetic induction heating the surface member 12 and the core member 11 from outside the surface member 12 provided on the outer peripheral surface of the core member 11 to melt at least one of facing regions 13a and 13b between the surface member 12 and the core member 11 with heat of the core member 11 thus heated. The electromagnetic induction heating is one of heating methods used in an electromagnetic cooker (IH cooking heater), high frequency welding, and the like, and utilizes a principle of generating variation in magnetic field (magnetic flux density) by alternating current flowing through a coil to generate induced current (eddy current) in a conductive substance provided in the magnetic field and generate heat from the conductive substance itself by resistance of the current. The core member 11 in the composite member 1 produced by the production method according to the present embodiment has magnetism higher than that of the surface member 12. The electromagnetic induction heating by an electromagnetic induction heating device increases heat quantity of the core member 11 rather than that of the surface member 12, so that temperature of the core member 11 is made higher than that of the surface member 12. It is thus possible to melt at least one of the facing regions 13a and 13b between the surface member 12 and the core member 11. In an exemplary case where the melting point of the surface member 12 is lower than that of the core member 11, heat generated from the core member 11 is transferred to the surface member 12 to melt the facing region (contact region) 13a in the surface member 12 with respect to the core member 11. Density of the induced current generated in the core member 11 thus electromagnetic induction heated is higher at a portion farther from the center of the core member 11 and closer to the surface thereof. The surface of the core member 11 is heated earlier (more concentratedly) than the inner portion of the core member 11. When the melting point of the core member 11 is lower than that of the surface member 12, melted is the surface of the core member 11 heated concentratedly (the facing region (contact region) 13b in the core member 11 with respect to the surface member 12). When current flowing through the electromagnetic induction heating device (the alternating current flowing through the coil) is set to have a high frequency, portions generating heat in the core member 11 can be located collectively at the surface thereof. In contrast, the inner portion of the core member 11 can generate heat uniformly when the current is set to have a low frequency. The electromagnetic induction heating device is thus preferably configured to appropriately vary the frequency of the current flowing through the electromagnetic induction heating device.

Examples of the electromagnetic induction heating device preferably used in the fusing step S3 include the device in a hollow cylindrical shape as illustrated in FIG. 4. An electromagnetic induction heating device 3 in the hollow cylindrical shape has a void 31 at the center. The core member 11 provided on the outer peripheral surface with the surface member 12 is located in the void 31 and is electromagnetic induction heated. After completion of electromagnetic induction heating for a predetermined period, the core member 11 provided on the outer peripheral surface with the surface member 12 is taken out of the void 31 at the center of the electromagnetic induction heating device 3 in the hollow cylindrical shape, or the electromagnetic induction heating device is stopped. The surface member 12 and the core member 11 are thus decreased in temperature and the melted regions are solidified to fix the surface member 12 and the core member 11 to each other.

The method for producing the composite member 1 according to the above embodiment includes the fusing step S3 of electromagnetic induction heating the core member 11 from outside the surface member 12 after the surface member 12 having magnetism lower than that of the core member 11 made of a conductive material is provided on the outer peripheral surface of the core member 11, to melt at least one of the facing regions 13a and 13b between the surface member 12 and the core member 11 with heat of the core member 11 thus heated (the facing region 13a in the surface member 12 with respect to the core member 11, the facing region 13b in the core member 11 with respect to the surface member 12, or the both thereof) and fuse the surface member 12 to the core member 11. The surface member 12 can be thus fused and fixed securely onto the outer peripheral surface of the core member 11 with no damage in shape, by thermal melting, of the outer surface of the surface member 12 provided around the surface of the core member 11. The composite member 1 can be thus provided with a function achieved by combining a material property of the member provided at the outer portion the composite member 1 (the surface member 12 fixed onto the outer peripheral surface of the core member 11) and a shape property of the outer surface of the composite member 1. The composite member 1 is produced by the above production method for spirally winding the linear material having corrosion resistance and serving as the surface member 12 around the outer peripheral surface of the core member 11 made of a long metal linear material. For example, the composite member 1 has corrosion resistance derived from the material property of the surface member 12 as well as excellent flexibility derived from the shape property of the outer surface of the composite member 1. Specifically, the composite member 1 produced by the above production method has flexibility higher than that of the composite member 1 produced by simply applying corrosion-resistant coating to the outer peripheral surface of the core member 11. In a case where the outer surface of the composite member 1 thus produced is permeated with lubricating oil, the lubricating oil enters a recess 14 (see FIG. 2) in the outer surface of the composite member 1, so that the composite member 1 can exhibit the function of retaining the lubricating oil for a long period of time.

Even in a case where a material hardly generated in the form of a liquid is selected for the surface member 12 upon provision of the surface member 12 on the outer peripheral surface of the core member 11, the surface member 12 formed into a linear shape or particle shapes can be fused and fixed onto the outer peripheral surface of the core member 11.

The above embodiment adopts the electromagnetic induction heating device 3 in the hollow cylindrical shape (having a ring shape in cross section) to be used in the fusing step S3 and locates the core member 11 provided on the outer peripheral surface with the surface member 12 in the void 31 at the center to perform electromagnetic induction heating. In other words, the electromagnetic induction heating is performed in the state where the surface member 12 provided on the outer peripheral surface of the core member 11 is surrounded. Heat is thus generated uniformly from the entire outer peripheral surface of the core member 11 to thermally melt uniformly the entire region to be thermally melted (the facing region 13a in the surface member 12 with respect to the core member 11, the facing region 13b in the core member 11 with respect to the surface member 12, or the both thereof). The surface member 12 provided around the outer peripheral surface of the core member 11 and the core member 11 can be bonded to each other with uniform fixing force with no variation.

In such a method for producing the composite member 1, the materials for the surface member 12 and the core member 11 are selected so that the surface member 12 has a melting point lower than that of the core member 11. The facing region (contact region) 13a in the surface member 12 with respect to the core member 11 can be thus melted earlier than the core member 11 with heat of the core member 11 electromagnetic induction heated. The core member 11 is not damaged in shape due to thermal melting but only the surface member 12 can be melted reliably, so that the surface member 12 can be fused and fixed onto the outer peripheral surface of the core member 11.

As exemplified in FIG. 5, in such a method for producing the composite member 1, the core member 11 can be alternatively formed so as to have a center portion 111 and a surface portion 112 made of different materials so that the surface portion 112 of the core member 11, corresponding to the facing region (contact region) 13b in the core member 11 with respect to the surface member 12, is thermally melted by electromagnetic induction heating. Even in such a configuration, the surface portion 112 of the core member 11 thus thermally melted is cooled and solidified, so that the surface member 12 and the core member 11 can be fused (fixed) firmly to each other.

Specifically, the center portion 111 of the core member 11 is made of a material having a relatively high melting point such as iron or stainless steel and the surface portion 112 of the core member 11 is made of a metal material having a melting point lower than that of the center portion 111 such as zinc or tin, for example. When the core member 11 thus configured is electromagnetic induction heated in the fusing step S3, the surface portion 112 having a melting point lower than that of the center portion 111 is thermally melted earlier. The material for the surface portion 112 is cooled and solidified, and the surface member 12 provided on the outer peripheral surface of the core member 11 (the surface member 12 provided on the surface portion 112 of the core member 11) is fixed to the core member 11. In such a method for producing the composite member, the material for the surface member 12 can be selected so that the facing region 13a in the surface member 12 with respect to the core member 11 is thermally melted, or the surface member 12 can be selected so that the facing region 13a in the surface member 12 with respect to the core member 11 is not thermally melted. The material for the surface member 12 can be thus selected from a wider range.

The core member 11 shown in FIG. 5 has a double layer structure including the center portion 111 and the surface portion 112. As exemplified in FIG. 6, the core member 11 can alternatively include the center portion 111 that has a plurality of layers 111a, 111b, and 111c made of different materials. The core member 11 has only to include the surface portion 112 made of a material having a melting point lower than that of the center portion 111 and have conductivity as a whole. The center portion 111 can be made of a material unlikely to conduct electricity and the surface portion 112 can be made of a conductive material. Alternatively, the center portion 111 can be made of a conductive material and the surface portion 112 can be made of a material unlikely to conduct electricity. The core member 11 needs to be heated preferentially rather than the surface member 12 when the core member 11 provided on the outer peripheral surface with the surface member 12 is heated by electromagnetic induction heating. The surface member 12 is thus made of a material having magnetism lower than that of the core member 11.

The method for producing the composite member 1 according to the present invention has been described. Its specific configuration is not limited to that of the embodiment described above. As exemplified in the block diagram of FIG. 7, the method for producing the composite member 1 can include the adhesive layer forming step S4 between the pretreatment step S1 and the surface member providing step S2 in the above embodiment.

The adhesive layer forming step S4 includes the applying step S41 and the drying step S42. The applying step S41 is executed to apply an adhesive having a melting point lower than that of the core member 11 to the outer peripheral surface of the core member 11. Examples of the method for applying an adhesive to the outer peripheral surface of the core member 11 can include a method for spraying an adhesive atomized using a spray gun or the like to the outer peripheral surface of the core member 11 to form an adhesive layer on the outer peripheral surface of the core member 11 (a spraying method) and a method for immersing the core member 11 in a reservoir containing an adhesive to form an adhesive layer on the outer peripheral surface (outer surface) of the core member 11 (a dipping method). The adhesive used in the adhesive layer forming step S4 is not particularly limited as long as the surface member 12 can be kept at a desired position on the outer peripheral surface of the core member 11 by its adhesive force. For example, the adhesive can be selected to have a melting point substantially not more than the melting point of the surface member 12 or a melting point not less than the surface member 12. When the adhesive is selected to have a melting point higher than that of the surface member 12, the adhesive preferably has high thermal conductivity so as to efficiently transfer heat of the heated core member 11 to the surface member 12. The adhesive can be selected to have various functions. In an exemplary case where the selected adhesive has excellent adiathermancy, the produced composite member can have the function exhibit by the core member, the function exhibit by the surface member, as well as the adiabatic function exhibit by the adhesive. The adhesive to be used can be a hot melt adhesive mainly made of a thermoplastic resin. When the hot melt adhesive is used, the hot melt adhesive is heated and melted to be then applied to the outer peripheral surface of the core member 11.

The drying step S42 is executed to dry the adhesive applied to the outer peripheral surface of the core member 11. For example, a blowing means blows a predetermined volume of wind to the core member 11 provided thereon with the adhesive to dry the adhesive. Alternatively, the blowing means can include a heating element to blow hot wind to the core member 11 provided thereon with the adhesive, or the adhesive can be air dried with no wind blowing thereto.

When the production method includes the adhesive layer forming step S4 (the applying step S41), prior to the surface member providing step S2, of applying an adhesive having a melting point lower than that of the core member 11 to the outer peripheral surface of the core member 11, assume that the surface member 12 has a melting point lower than that of the core member 11 and the adhesive applied by an adhesive layer forming means 5 has a melting point substantially not more than the melting point of the surface member 12. In this case, the adhesive provided in the facing region 13a in the surface member 12 with respect to the core member 11 and between the surface member 12 and the core member 11 can be melted by electromagnetic induction heating the core member 11, and the surface member 12 can be thus fixed to the core member 11 more firmly. Specifically, when the surface member 12 is made of a linear material spirally wound around the outer peripheral surface of the core member 11 or is made of particles or fibers sprayed and provided on the outer peripheral surface of the core member 11, the melted adhesive enters gaps between adjacent portions of the linear material or the adjacent particles (the surface member 12), so that the surface member 12 can be fixed securely to the core member 11. When the surface member 12 has a melting point higher than that of the core member 11, the adhesive provided between the surface member 12 and the core member 11 is melted by heating the core member 11. The adhesive thus melted enters gaps between the adjacent portions of the surface member 12, so that the surface member 12 and the core member 11 can be fixed securely to each other. Even when the adhesive has a melting point higher than that of the surface member 12, heat of the core member 11 is transferred to the surface member 12 through the adhesive layer to melt the facing region 13a in the surface member 12 with respect to the core member 11. When the melted facing region 13a is cooled, the surface member 12 can be fixed onto the core member 11 with the adhesive layer being interposed therebetween.

The adhesive layer forming step S4 to be performed prior to provision of the surface member 12 on the outer peripheral surface of the core member 11 includes the drying step S42 of drying the adhesive applied to the outer peripheral surface of the core member 11. The surface member 12 can be thus provided on the outer peripheral surface of the core member 11 in a state where the adhesive has no adhesive force. The surface member 12 can be alternatively provided on the outer peripheral surface of the core member 11 even with active adhesive force of the adhesive, in other words, even in a state where the adhesive is not dried. In a case where the surface member 12 is provided on the outer peripheral surface of the core member 11 with the adhesive being not dried but in a liquid state or a semiliquid state, the adhesive in the liquid state (or the semiliquid state) may leak from around the provided surface member 12 and remain on the outer surface of the composite member 1 finally obtained. Otherwise, the adhesive in the liquid state (or the semiliquid state) may flow along the outer peripheral surface of the core member 11 and fail to be distributed with uniform thickness on the outer peripheral surface of the core member 11. If electromagnetic induction heating is performed in such a case, fixing force between the surface member 12 and the core member 11 may be decreased at a portion on the surface of the core member 11 to which the adhesive is applied thinly when the adhesive and/or the facing region 13a in the surface member 12 with respect to the core member 11 is melted and the surface member 12 is fixed to the core member 11. In contrast, when the adhesive applied to the outer peripheral surface of the core member 11 is dried prior to provision of the surface member 12 on the outer peripheral surface of the core member 11 and the surface member 12 is then provided on the outer peripheral surface of the core member 11, the adhesive can be effectively prevented from leaking or being distributed with ununiform thickness as described above. The adhesive can be reliably prevented from remaining on the outer surface of the composite member 1 finally obtained, or generation of a portion of less fixing force between the surface member 12 and the core member 11 can be prevented reliably.

The embodiment described above adopts the electromagnetic induction heating device 3 in the hollow cylindrical shape illustrated in FIG. 4 to be used in the fusing step S3. The device is not particularly limited to this configuration but can have any shape as long as the device can vary the magnetic field (magnetic flux density) of the core member 11 provided with the surface member 12 in the surface member providing step S2 to generate eddy current in the core member 11. For example, the electromagnetic induction heating device 3 can have a plate shape such as that used in an electromagnetic cooker (IH cooking heater) and the core member 11 provided with the surface member 12 can be located close to the electromagnetic induction heating device 3 in the plate shape so as to be heated.

Described in the above embodiment as the method for providing the surface member 12 on the outer peripheral surface of the core member 11 in the surface member providing step S2 (the covering step) is the method for spirally winding the surface member 12 made of a linear material around the outer peripheral surface of the core member 11 to cover the outer peripheral surface of the core member 11 with the surface member 12 (the method using the covering device 2). However, the method for providing the surface member 12 on the outer peripheral surface of the core member 11 (the covering step) is not limited particularly to this method. For example, the above embodiment can alternatively adopt the method for spirally winding the surface member 12 having a linear shape or a belt shape on the outer peripheral surface of the core member 11 by turning the core member 11 to cover the outer peripheral surface of the core member 11 with the surface member 12. When the surface member 12 having a belt shape is wound to be provided on the core member 11, the adjacent portions of the surface member 12 may be or may not be overlapped with each other in terms of a winding pitch. When the core member 11 has a bar shape with a relatively large diameter, the method for spirally winding the surface member 12 in the belt shape on the outer peripheral surface of the core member 11 by turning the core member 11 is adopted so that the surface member 12 can be provided efficiently on the core member 11. Alternatively, the outer peripheral surface of the core member 11 can be covered with the surface member 12 by spraying the surface member 12 in particle shapes or fiber shapes to the outer peripheral surface of the core member 11. When the surface member 12 in the particle shapes or the fiber shapes is sprayed to be provided on the outer peripheral surface of the core member 11, in a preferred example, the outer surface of the core member 11 is electrified to have a plus electrical charge and the surface member 12 in the particle shapes or the fiber shapes is electrified to have a minus electrical charge so that the surface member 12 in the particle shapes or the fiber shapes adheres to the outer peripheral surface of the core member 11. Alternatively, the method for producing the composite member 1 preferably includes only the applying step S41 in the adhesive layer forming step S4 (without including the drying step S42) so that the surface member 12 in the particle shapes or the fiber shapes is sprayed to the adhesive layer not yet dried.

DESCRIPTION OF REFERENCE SIGNS

S1 Pretreatment step
S2 Surface member providing step
S3 Fusing step
S4 Adhesive layer forming step
S41 Applying step
S42 Drying step
1 Composite member
11 Core member
111 Center portion of core member
112 Surface portion of core member
12 Surface member
13a Facing region in surface member with respect to core member
13b Facing region in core member with respect to surface member
14 Recess
2 Covering device 21 Spool
3 Electromagnetic induction heating device
31 Void

The invention claimed is:

1. A method for producing a composite member including a core member made of a conductive material and a surface member made of a linear material and fixed to an outer peripheral surface of the core member, the method comprising:
   a surface member providing step of providing the surface member having magnetism lower than magnetism of the core member on the outer peripheral surface of the core member; and
   a fusing step of electromagnetic induction heating the core member from outside the surface member to melt at least one of facing regions between the surface member and the core member with heat of the heated core member and fuse the surface member to the core member,
   wherein the surface member providing step includes a covering step of winding the surface member around the outer peripheral surface of the core member to cover the outer peripheral surface of the core member with the surface member, and
   the surface member made of the linear material provided around the surface of the core member is fused and fixed onto the outer peripheral surface of the core member with no damage in shape of the outer surface of the surface member by thermal melting.

2. The method for producing the composite member according to claim 1, wherein the surface member has a melting point lower than a melting point of the core member.

3. The method for producing the composite member according to claim 2, the method comprising, prior to the surface member providing step, an adhesive layer forming step of applying an adhesive having a melting point lower than a melting point of the core member to the outer peripheral surface of the core member.

4. The method for producing the composite member according to claim 3, wherein the adhesive layer forming step includes a drying step of drying the adhesive applied to the outer peripheral surface of the core member.

5. The method for producing the composite member according to claim 1, wherein the core member has a center portion and a surface portion, and the surface portion of the core member is melted with heat of the core member electromagnetic induction heated to fuse the surface member to the core member.

6. The method for producing the composite member according to claim 5, the method comprising, prior to the surface member providing step, an adhesive layer forming step of applying an adhesive having a melting point lower than a melting point of the core member to the outer peripheral surface of the core member.

7. The method for producing the composite member according to claim 6, wherein the adhesive layer forming step includes a drying step of drying the adhesive applied to the outer peripheral surface of the core member.

8. The method for producing the composite member according to claim 1, the method comprising, prior to the surface member providing step, an adhesive layer forming step of applying an adhesive having a melting point lower than a melting point of the core member to the outer peripheral surface of the core member.

9. The method for producing the composite member according to claim 8, wherein the adhesive layer forming step includes a drying step of drying the adhesive applied to the outer peripheral surface of the core member.

* * * * *